United States Patent [19]
Grosselin et al.

[11] Patent Number: 5,986,137
[45] Date of Patent: Nov. 16, 1999

[54] ALLYLATION REAGENT AND PROCESS FOR ALLYLATING A NUCLEOPHILE

[75] Inventors: Jean-Michel Grosselin, Francheville; Hubert Kempf; Jean-Pierre LeCouve, both of Mulhouse, all of France

[73] Assignee: Rhodia Chimie, Courbevoie, France

[21] Appl. No.: 09/097,155

[22] Filed: Jun. 12, 1998

Related U.S. Application Data

[62] Division of application No. 07/739,053, Aug. 2, 1991.

[30] Foreign Application Priority Data

| Aug. 2, 1990 | [FR] | France | 90 09886 |
| Aug. 2, 1990 | [FR] | France | 90 09887 |
| Aug. 2, 1990 | [FR] | France | 90 09888 |
| Aug. 2, 1990 | [FR] | France | 90 09889 |

[51] Int. Cl.$^6$ ................................................ C07C 213/00
[52] U.S. Cl. .............................. 564/399; 568/657; 568/658
[58] Field of Search ............................... 564/399; 568/657, 568/658

*Primary Examiner*—Samuel Barts
*Attorney, Agent, or Firm*—Finnegan, Henderson, Farabow, Garrett & Dunner, L.L.P.

[57] ABSTRACT

A process and reagent for allylating a nucleophile preferably of formula (V).

$$(R)_n\text{Ar}—Y—H \qquad (V)$$

The nucleophile is reacted with a reagent containing an allyl derivative and a catalyst in an aqueous phase containing at least lone element of group VIII of the Classification of the elements. A water-soluble phosphine may also be present in the reagent, and the reagent may also contain at least one organic phase.

29 Claims, 1 Drawing Sheet

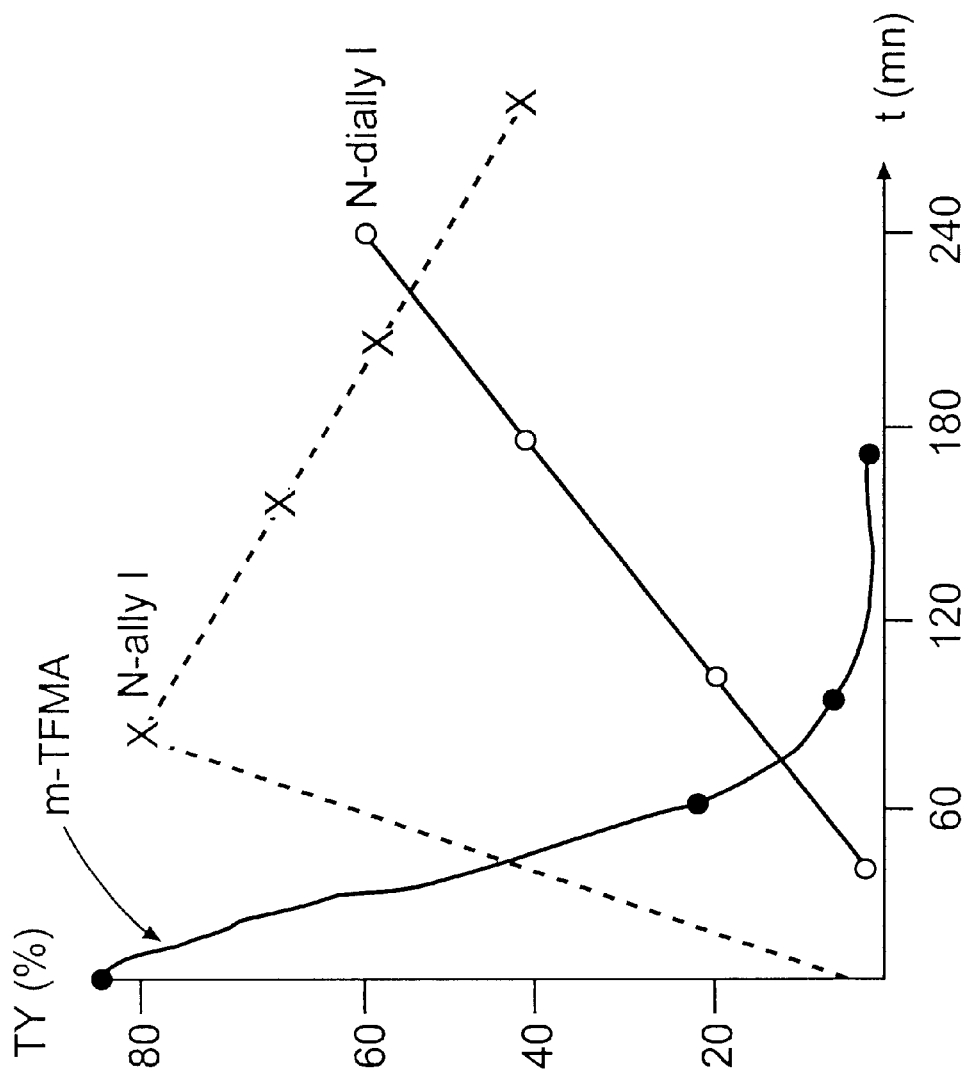

ALLYLATION REAGENT AND PROCESS FOR ALLYLATING A NUCLEOPHILE

This application is a Divisional of 07/739,053 filed Aug. 2, 1991.

The present invention relates to a process for the synthesis of allyl compounds. It relates more particularly to the allylation of anilines such as meta-trifluoromethylanilines.

N-Allylations of amides, and in particular of anilides, anilines and phenol, are often difficult and necessitate the use ilof reagents such as alkyl halides, which are expensive and generate large amounts of saline wastes.

The N-allylation of anilides is an important step in the synthesis of many compounds. The reaction can lead either to mono- or polyallylations, which can be of paramount importance when it is desired to obtain one type of allylation which is more selective with respect to the others. For example, during the synthesis of N-allyl-N-dichloroacetyl-meta-trifluoromethylanilide, an intermediate in the synthesis of an important herbicide, the step of allylation of meta-trifluoromethylaniline (m-TFMA) has to be a mono-allylation which is as selective as possible with respect to the diallylation.

One of the objects of the present invention is to provide a process which is capable of allylating anilides even when they are deactivated by electron-attracting groups.

Another object of the present invention is to provide a process which is capable of allylating anilines using inexpensive and readily accessible reagents.

Another object of the present invention is to provide a process which is capable of allylating anilines even when the anilines are deactivated by electron-attracting groups.

Another object of the present invention is to provide a process which is capable of allylating phenols even when the latter are deactivated by electron-attracting groups.

Another object of the present invention is to provide a process which is capable of allylating any nucleophilic substrate, in particular a nonionic nucleophilic substrate (such as organometallic compounds), even one as poor as amides.

Another object of the present invention is to provide an allylation reagent which is usable for the above process.

These and other objects which will become apparent hereinafter are achieved by means of a process employing an allylating reagent containing at least:
- an allyl derivative, preferably allyl ether, a source of allyl ether, or allyl alcohol, and
- a catalyst containing at least one element of group VIII of the Periodic Classification of the elements (Fe, Co, Ni, Ru, Rh, Pd, Os, Ir, Pt) (see. Bull. Soc. Chim. 1966 No. 1 supplement).

The allyl derivative is preferably of formula (III):

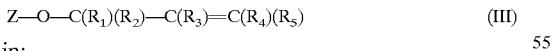

wherein:
- $R_1$ represents a hydrogen or an alkyl radical, preferably containing 1 or 2 carbon atoms;
- $R_2$ represents a hydrogen or an alkyl radical, preferably containing 1 or 2 carbon atoms;
- $R_3$ represents a hydrogen or an alkyl radical;
- $R_4$ represents a hydrogen or an alkyl radical;
- $R_5$ represents a hydrogen or an alkyl radical;
- wherein the term "alkyl" includes the term "aryl" and Z represents a hydrogen atom or a residue derived from an alcohol (including phenols) by removal of a hydroxyl group,
- a catalyst containing at least one element of group VIII of the Periodic Classification of the elements.

The ether may be made "in situ" from alcohol(s). It is preferable that the stationary content of ether is such that the ether/alcohol ratio is greater than 1/2%, more preferably greater than 5% and most preferably between 10% and 20%.

The term alkyl is employed with the meaning given in the *Duval Dictionary of Chemistry*, with the additional feature that it can also include an aryl group.

It is preferable that at least 2, more preferably 3 and most preferably 4 of the radicals R to R have at most two carbon atoms; however, at least one of the radicals $R_1$ to $R_5$ may be such that the allyl alcohol is a heavy alcohol, for example of the aromatic series, of the terpine type or of the steroid series.

Thus, at least 1 radical and at most 3 radicals $R_1$ to $R_5$ may be polycyclic aryl radicals, fused or otherwise, homo- or heterocyclic. Said reagent can, in the process according to the present invention, be brought into contact with any nucleophilic substrate, in particular a non-anionic nucleophilic substrate. The anionic species are, for example, those which are supposedly active in organometallic compounds, especially in the case of synthesis via carbanions. The species rendered nucleophilic by stripping out mobile hydrogen to form a carbanion are supposedly anionic, including phenols and anilines deactivated by at least one electron-attracting substituent on, or by the presence of a hetero atom in, the aromatic ring-system.

The reaction also gives very good results when the aromatic ring-system is deactivated by the presence of attracting group(s).

A deactivated aryl radical is one depleted of electrons, and with an electron density at most equal to that of benzene, or at most similar to that of a halobenzene. This depletion may be due to the presence of a hetero atom in the aromatic ring when it has six members, such as in pyridine or quinoline.

Naturally, the electron depletion may also be caused by electron-attracting groups; the low electron content may be due to both of these causes.

Thus, the deactivated aryl preferably carries at least one substituent selected from groups which attract by a donor effect or by a mesomeic effect as defined in the reference work in organic chemistry "Advanced Organic Chemistry" by M. J. MARCH, 3rd edition, published by WILEY, 1985; see, in particular pp. 17 and 238. Examples of attracting groups are $NO_2$, $CF_3$, CN, COX (X=Cl, Br, F, OR), CHO, Cl, Br.

The allylation gives particularly good results when the process is applied to a compound of formula (V):

wherein:
- Ar represents a monocyclic aromatic radical which may be homocyclic or heterocyclic or Ar represents a polycyclic aromatic radical which may be fused or non-fused and may also be homo- or heterocyclic,
- R represents at least one substituent selected independently from hydrogen, chlorine, bromine, saturated or unsaturated and optionally substituted linear, branched or cyclic alkyl (including aryl) radicals, ether, and optionally substituted radicals selected from alkoxy, aryloxy, amino, hydroxyl, carboxylate, acyloxy, ester, amido, nitrile and acid radicals,
- n is an integer greater than or equal to 1, preferably equal to 1, 2, 3 or 4,
- Y represents a chalcogen atom, preferably an oxygen atom, or a group NR' with R' representing a light acyl having 1 to 10, preferably 1 to 6 and more preferably 2 to 5 carbon atoms, and optionally polyhalogenated, preferably mono-, di- or trihalogenated, a light alkyl (including aryl) having 1 to 10, and preferably 1 to 6, carbon atoms, or a hydrogen atom.

Particularly useful are the deactivated anilines of formula II:

A—Ar—N—H$_2$ (II)

wherein:

A represents a substituent as defined by R, preferably an attracting group, in particular perfluoroalkyl, or a hydrogen atom;

Ar has the same meaning as above and the phenols having formula IV:

(R)$_n$Ar—O—H (IV)

wherein:

Ar, R and n have the same meaning as above.

Thus, the reaction can also give very good results when the aromatic ring is deactivated by the presence of attracting group(s). The total number of carbon atoms in the substrates rarely exceeds 50, although there is no contra-indication for heavier substrates.

The following are preferable reaction conditions for carrying out the reaction. The temperature is preferably above room temperature and below or equal to the refluxing temperature. When it is appropriate to work at other temperatures, a temperature of between 100° C. and 300° C. may be used, preferably between 100° C. and 200° C., although the temperatures are given by way of example and should not be considered as limiting.

The pressure used is preferably the equilibrium pressure of the reagent at the temperature of use. A higher pressure may also be used.

The reaction is preferably conducted in the absence of an oxidizing agent, particularly oxygen, which has the drawback of oxidizing phosphines or equivalent compounds. The reactions are preferably conducted under an inert atmosphere (such as a rare gas, nitrogen, etc.), on previously outgassed reactants if the phosphines or equivalent compounds used are especially susceptible to degradation.

The allylation can be, in particular, an N, O or C allylation. When the allyl radical is palindromic, the direction of allylation is of little importance. Otherwise, as a guide, the allylation takes place essentially according to the rules known to those skilled in the art, at the 1- or 3-position of the allyl radical, in which rules the hindrance plays an important part (allylation via the less hindered side).

When the ether is a phenol ether, the preponderant allylation is an internal C-allylation at the ortho position. Thus, when the allylation is carried out on a phenol (an alcohol in the broad sense), the phenol ether obtained may rearrange by an internal C-allylation at the ortho position, liberating the phenol function for a second allylation.

The metals giving the best catalytic results are the platinum ore metals; however, it may be economically advantageous to use lighter metals on a,ccount of their much lower cost. In the platinum ore metal family, each metal has specificities which makes it more or less advantageous according to the case.

As an example, in the allylation of anilides, the metal generally giving the best result is palladium, usually activated by at least one pnictine. However, when the anilide is derived from an alpha-halogenated acid or, generally speaking, when the substrate has an activated halogen, palladium catalysis can lead to many byproducts. In these cases, it has been demonstrated that the use of platinum, preferably activated by at least one pnictine (arsine, stibine, phosphine, etc.) gives results which are both significant and selective.

In the case of the allylation of bi- or polysubstitutable compounds, it is desirable not to increase the kinetics of the reaction excessively, particularly when carrying out only a mono- or oligoallylation. In these situations, agents may be added which retard the reaction, such as antimony trioxide or bismuth trioxide.

When the selectivity between oligo- and polyallylation is not sufficient, it is possible to improve selectivity by varying the excess of allyl ether, or its derivative, relative to the substrate, for example by limiting the stoichiometric excess with respect to the desired reaction to ½, preferably to ¼ and more preferably to 1/10, or alternatively by working with an excess of substrate.

Thus, the present invention constitutes an improvement over the prior art by providing a spectrum of reagents which can have varied subtle differences which can be used and adapted to many different cases.

The catalytic features of the elements of group VIII may be modified by coordinating agents. Such agents may be selected from organic derivatives of the elements of group V which are known to have coordination capacity, such as phosphines, arsines, stibines or nitriles, in particular aromatic nitrites such as benzonitrile, and oxygen-containing organic compounds of these elements of group V, for example, phosphorous acid esters, phosphonates and phosphinates. Preferred elements of group V are those whose period is of a higher rank than that of the period of nitrogen.

The coordinating agents are advantageously hydrocarbon derivatives of the elements of group V. The hydrocarbon derivatives of the elements of group V are derived from nitrogen such as amines, from phosphorus such as phosphines, from arsenic such as arsines and from antimony such as stibenes. These compounds are, by analogy with the term pnictide, designated in the present description by the term pnictines. They are preferably selected from the hydrocarbon derivatives of phosphorus such as phosphines.

The catalyst may contain, as a pnictine, a trialkylphosphine, preferably a triphenylphosphine. The phosphine and the metal of group VIII are preferably in the form of tetrakis(phosphine)-metal.

Some weakly nucleophilic substrates are slow to react; thus in order to accelerate the allylation, a small amount of stannous salt, such as SnCl$_2$, may be added. At most the salt is added in a, quantity equal to the amounts of the metal of group VIII, but preferably approximately tenfold less in molar terms of the stannous salts.

It should be emphasized that one of the important objects of the present invention is to provide a reagent which permits the desired allylation, especially a monoallylation. The presence of stannous salts strongly promotes the diallylation of anilines.

For this reason, it is preferable that the catalyst has as low a tin content as possible. The mole ratio of tin to the element of group VIII of the Periodic Classification of the elements is preferably less than $10^{-2}$, and more preferably less than $10^{-4}$.

In the case, to which the invention is more especially directed, where it is desired to carry out an N-monoallylation on an aniline deactivated by at least one electron-attracting substituent, alkylation, including allylation, is a special case which virtually failed to proceed. This makes the results obtained by carrying out the present invention all the more surprising.

However, the compounds of group V B (N, P, As, Sb, Bi) may also be present in the form of trivalent oxides, such as arsenious oxide, which are not excluded from the above compounds and can give better results, not functioning to the detriment of monoallylation.

In general, these compounds significantly increase the kinetics of the reaction. In this case, the element of group V B is generally arsenic.

The catalyst may contain, as compounds of the elements of group V, a trialkylphosphine, preferably a triphenylphosphine. The phosphine and the metal of group VIII are preferably in the form of tetrakis(phosphine)-metal.

In the context of the present invention, a metal catalyst may be used in elemental form (oxidation number zero) or in oxidized form. These catalysts can take the form of salts, oxides or complexes. The catalysts can be used in aqueous phase. Examples of the salts, oxides and complexes of the metals mentioned above, in the oxidation state II, are palladium chlorides, palladium acetate and palladium chloride complexed with benzonitrile. The co-anions are of little importance, whereas the cations are of significance.

An example of a complex of the metals in the oxidation state zero is (dibenzylideneacetone)palladium.

It is preferable to use an amount of catalyst such that the mole ratio of the metal catalyst to the compounds of the elements of group V, which are in the form of coordinating agents, often designated by the term ligand, is between 2:1 and 100:1, and preferably from 4:1 to 30:1. The mole ratio of the oxides of group V to the metal catalyst is generally between 1:100 and 100:1 preferably from 5:100 to 10:1 and most preferably approximately 1:1.

The reaction can take place in, and the reagent contain, any solvent, including those capable of acting as a solvent A or B as described later, such as:

benzene and aromatic solvents, alkanes having at least 6 carbon atoms, water, acetonitrile, benzonitrile, dimethylformamide, N-methylpyrrolidone, nitrobenzene.

However, when the reaction is performed in an aprotic solvent, in particular a nonaqueous solvent, and/or when the allyl derivative contains an ether group, it is preferable to use weakly basic solvents having a donor number less than that of tetrahydrofuran (20), preferably at most equal to that of diethyl ether, more preferably 10 and most preferably 5. The inhibitory character of the solvents may be used to increase the selectivity of the oligo- and monoallylation; preferably the solvent is used in a molar amount less than that of the substrate.

It is, in this case, desirable to avoid solvents including the last 4 on the list given as an example (or, more precisely, as a paradigm in the classical and grammatical sense of the term). The absence of a solvent or the use of the substrate or of a component of the reagent may then be a good approach. It should be recalled that the donor number, sometimes designated by the acronym DN, is defined by the value of the change in enthalpy delta-H due to the association of the solvent with antimony pentachloride in dilute methylene chloride medium.

The amount of solvent used is such that the concentration of the metal of group VIII is greater than $10^{-5}$ M, and preferably from $10^{-2}$ to $10^{-3}$ M in the solvent. This preference applies to the aqueous phase in the event of use of the latter alone or in a two-phase system.

Preferred are the reactions without a solvent or in which the substrate is the solvent, those in which the solvent is the allylating agent, in particular the allyl derivative, and those in which the solvent is an aqueous phase.

The reaction may also use water-soluble pnictines as pnictines, and use an aqueous reagent.

To render the coordinating agents, and in particular the pnictines, water-soluble, polar groups imparting water-solubility may be grafted, taking care not to create in this manner nucleophiles which would be liable to interfere with the reaction.

It is possible to graft neutral groups such as polyols but, in view of the strong lipophilicity of pnictines, it is preferable that the grafted groups are ionic, cationic such as quaternary ammonium groups, or anionic such as any group constituting the associated base of acids, preferably strong acids. In the latter case, carboxyl, sulfonic or phosphonic groups are examples.

French Patent No. 2,366,237 or French Patent No. 2,549, 840, which are hereby incorporated by reference, relate to groups used for modifying phosphines.

Water-soluble phosphines include the soluble triphenylphosphinetrisulfonates $P(C_5H_4—SO_3—)_3$, for example of alkali metals, and those of formula $P(C_5H_4—CO_2H)_3$, preferably in anionic form.

A preferred embodiment of the present invention uses a two-phase system in which one of the two liquid phases is an aqueous phase in which the metal of group VIII is solubilized in the aqueous phase by a water-soluble phosphine or equivalent compound. This technique greatly facilitates recovery and recycling of the catalyst, which recycling is one of the key parameters of the profitability of this type of process on account of the ever-increasing cost of platinum ore metals. Moreover, the yields are not significantly impaired by the use of two liquid phases.

Unexpectedly, the use of an aqueous phase can enable the monoallylation to be accelerated considerably without a concomitant acceleration of poly- and, in particular, diallylation. It is thus much easier to perform a selective oligoallylation relative to a polyallylation. When the selectivity provided by the use of the aqueous phase is not sufficient, it is possible to vary the excess of allyl derivative, for example of allyl ether or its derivative, relative to the substrates. The excess alkyl derivative may be varied by limiting the stoichiometric excess with respect to the desired reaction to ½, preferably to ¼ and more preferably to ⅒, or alternatively by working with an excess of substrate.

In another preferred embodiment of the present invention, it is possible to use a two- or multiphase system in which one of the liquid phases is an aqueous phase. In particular, when the substrate, the allyl derivative such as the allyl ether and/or the end product are only slightly soluble in the aqueous phase, it is possible to perform the reaction, either without the addition of a solvent in a multiphase system, or by adding an intermediary solvent B, or by adding a solvent A, or by adding an intermediary solvent B and solvent A.

The solvents A are organic solvents selected in such a way that they dissolve at least 1%, and preferably at least 2%, by mass of the substrate, and are sufficiently hydrophobic not to be miscible with water in all proportions.

It is preferable that water can dissolve at most only 10% of solvent A, and preferably at most 1%, by mass, even in the presence of the substrate as an intermediary solvent.

It is preferable that solvent A can dissolve at most only 10% of water, and preferably at most 1%, by mass, even in the presence of the substrate as an intermediary solvent.

The solvents A can be mixtures, including petroleum cuts. Under the working conditions, the solvents A must be inert with respect to the substrates and reactants used.

The preferred families of solvents A are selected from the group consisting of hydrocarbons, aromatic derivatives, ethers, esters and halogenated solvents. Preferably, these solvents should be less nucleophilic than the substrates, so as not to interfere with the reaction, unless the substrate is in excess in order to play a solvent role.

Examples of these families are halogenated derivatives such as dichloromethane, 1,2-dichloroethane and 1,1,1-trichloroethane, aromatic derivatives such as toluene and halogenated aromatic derivatives such as chlorobenzene, esters such as ethyl acetate and isopropyl acetate, and ethers such as tert-butyl methyl ether, anisole, and heavy alcohols, which satisfy the constraints of immiscibility as specified above.

For reasons of industrial economy, it is preferable that solvent A is distilled at atmospheric pressure or under coarse or higher vacuum.

If the substrates are not water-soluble, an intermediary solvent B may be added to solvent A, which solvents can be mixtures whose role will be to solubilize the substrate and/or, where appropriate, the allyl derivative or the specific allyl ether in the aqueous phase, and which will distribute between the aqueous and organic phases when the latter exists initially.

It is preferable that the water can dissolve at least 1/10 of intermediary solvent B, and preferably at least 1/3, by mass, even in the presence of the catalyst with its coordinating agents.

The intermediary solvent is preferably added in a sufficient amount for the amount of substrate and/or, where appropriate, the allyl ether or other allyl derivative, soluble in the aqueous phase, to be at least of the same order of magnitude (within a factor of ten) as the amount of catalyst present in the aqueous phase at the beginning of the reaction.

Subject to the above preferences, solvents which are usable as intermediary solvents, are water-soluble solvents of the alcohol, nitrile, ether (especially cyclic), acid, sulfone, sulfoxide, amide, alkyl phosphate, alkyl phosphonate, alkyl phosphinate, phosphine oxide and ketone types, or even of the type comprising an amine which is not nucleophilic, in particular, through a steric effect.

It is also possible to select solvent A such that it also plays the part of an intermediary solvent B. In this case, solvents are used which possess a polar function of the type possessed by the intermediary solvents, and which have a lipophilic chain selected in such a way that water dissolves said intermediary solvent in the proportion of approximately 1/100 to 1/10 by mass.

Solvent A and/or solvent B, depending on the case, can be the allyl ether or derivative.

The present invention also contemplates the replacement of said allyl derivative by one of the derivatives of allyl alcohol capable of giving an ether or an alcohol in situ under the conditions of the allylation reaction. Further the present invention contemplates use as a source of the allyl radical of a mixture of allyl ether and/or alcohol with other precursors of the allyl radical.

Another objective of the present invention is an allylation reagent employing a reagent which is as inexpensive as allyl ethers, and in particular employing the above reagent.

This objective is achieved by means of the allylation reagent, which contains:

an allyl alcohol or allyl ether derivative of the formula (III):

$$Z\text{—}O\text{—}C(R_1)(R_2)\text{—}C(R_3)\!\!=\!\!C(R_4)(R_5) \quad (III)$$

wherein:

$R_1$ represents a hydrogen or an alkyl radical, preferably containing 1 or 2 carbon atoms;

$R_2$ represents a hydrogen or an alkyl radical, preferably containing 1 or 2 carbon atoms;

$R_3$ represents a hydrogen or an alkyl radical;

$R_4$ represents a hydrogen or an alkyl radical;

$R_5$ represents a hydrogen or an alkyl radical, and

Z represents a hydrogen atom or a residue derived from an alcohol by removal of a hydroxyl group, a catalyst containing at least one element of group VIII of the Periodic Classification of the elements.

The allylation reagent may or may not contain a solvent, and may or may not contain an aqueous phase.

Another reagent according to the present invention contains:

an aqueous phase;

an allyl alcohol or one of its derivatives;

a catalyst containing at least one element of group VIII of the Periodic Classification of the elements, said element of group VIII of the Periodic Classification being maintained in the aqueous phase by complexing with at least one water-soluble coordinating agent (or ligand).

This reagent may or may not contain a solvent. A solvent A may be present which is not completely miscible with the aqueous liquid phase. A solvent B may be present providing, in the aqueous phase, for a minimal solubility of the lipophilic substrates.

Said allyl alcohol or one of its derivatives is preferably selected from the derivatives of formula (III'):

$$Z'\text{—}O\text{—}C(R_1)(R_2)\text{—}C(R_3)\!\!=\!\!C(R_4)(R_5) \quad (III')$$

wherein:

$R_1$, $R_2$, $R_3$, $R_4$, and $R_5$ have the same definition as above and where Z' represents an acyl radical, preferably having at most carbon atoms, or preferably hydrogen.

The whole invention will be described more completely by means of the examples which follow, which must in no case be considered to be limiting.

In the examples which follow, the following definitions apply:

DC=the degree of conversion of the starting material $$DC = \frac{\text{number of moles of material converted}}{\text{number of moles of initial material}}$$

TY = the yield with respect to the initial material $$TY = \frac{\text{number of moles of final product}}{\text{number of moles of initial material}}$$

CY = the yield with respect to the material converted $$CY = \frac{\text{number of moles of final product}}{\text{number of moles of material converted}}$$

GENERAL PROCEDURE

The reactants, solvents and catalysts were introduced in the stated proportions into the container in which the reaction took place.

This operation was carried out in a glove box placed under nitrogen, the ingredients being outgassed beforehand in order to remove oxygen. When the boiling point of the reaction mixture was above the test temperature, either a reactor or a sealed tube or a Schott tube was used. Where not otherwise specified, a sealed tube was used.

When the temperature was above the boiling point, one of the two tubes was used. Where not otherwise specified, a sealed tube was used.

The other reaction conditions are specified in the examples which follow. Except where otherwise stated, the reactants used were as follows:
  allyl alcohol;
  palladium;
  triphenylphosphine.

The allyl ether used was $(H_2C=CHCH_2)_2O$ unless phenol was present at which point the allyl ether was an ether of allyl and phenol.

EXAMPLE 1

Reactants
m-TFMA: 2 mmol (m-TFMA=meta-trifluoromethylaniline)
$Pd(P\phi_3)_4$: 2 mol %
4 h at 90° C. with stirring
1 equivalent allyl ether: 2 mmol
RESULTS

| $As_2O_3$ | DC allyl ether | DC (m-TFMA) | CY (N-Allyl) | CY (Diallyl) |
|---|---|---|---|---|
| 0% | 49 | 46 | 87 | 16 |
| 5% | 91 | 100 | 20 | 79 |

EXAMPLE 2 m-TFMA: 2 mmol
$Pd(P\phi_3)_4$: 2 mol %
4 h at 90° C. with stirring ½ equivalent allyl ether: 1 mmol
RESULTS

| $As_2O_3$ | DC allyl ether | DC (m-TFMA) | CY (N-Allyl) | CY (Diallyl) |
|---|---|---|---|---|
| 0% | 89 | 68 | 80 | 12 |
| 4.5% | 99 | 79 | 78 | 21 |

EXAMPLE 3

Study of $Pd(P\phi_3)_4$ and $Pt(P\phi_3)_4$

Reactants
m-TFMA: 2 mmol
Allyl ether: 1 mmol
Catalyst: 2 mol %
4 h at 90° C. with stirring
RESULT

| Catalyst | DC allyl ether | DC (m-TFMA) | CY (N-Allyl) | CY (Diallyl) |
|---|---|---|---|---|
| $Pt(P\phi_3)_4$ 4.1% | 32 | 14 | 74 | 12 |
| $Pd(P\phi_3)_4$ 4.5% | 89 | 68 | 80 | 12 |

Comment
$Pd(P\phi_3)_4$ was markedly more reactive than $Pt(P\phi_3)_4$ for the same selectivity.

EXAMPLE 4

Influence of $B_2O_3$

REACTION
m-TFMA+allyl ether→N-allyl-TFMA+diallyl-TFMA
Reactants
m-TFMA: 2 mmol
$Pd(P\phi_3)_4$: 2 mol %
4 h at 90° C. with stirring
Allyl ether: 6.5 mmol
RESULT

| $B_2O_3$ | DC allyl ether | DC (m-TFMA) | CY (N-Allyl) | CY (Diallyl) |
|---|---|---|---|---|
| 5% | 69 | 100 | 2 | 99 |

EXAMPLE 5

Comparative Reactivity of Allyl Ether and Alcohol
REACTION
  m-TFMA+1-propanol→N-allyl-TFMA+N,N-diallyl-TFMA 1-Propenol=allyl alcohol
Reactants
m-TFMA: 2 mmol
$Pd(P\phi_3)_4$: 2%
$As_2O_3$: 1.1%
1 h at 90° C.
RESULT

| Allylating agent | DC (m-TFMA) | CY (N-Allyl) | CY (Diallyl) |
|---|---|---|---|
| Allyl alc. 11.5 mmol | 78 | 65 | 31 |
| Allyl eth. 11.5 mmol | 99 | 19 | 82 |

Furthermore, the allyl alcohol and ether were assayed:

| DC (allyl alcohol) = 74 | CY (allyl ether) = 31 |
|---|---|
| DC (allyl ether) = 35 | CY (allyl alcohol) = 2 |

EXAMPLE 6

Comparative Reactivity of Allyl Ether and Alcohol
Reactants
m-TFMA: 2.1 mmol
$Pd(P\phi_3)_4$: 2.2%
15 min at 90° C.
RESULT

| Allylating agent | DC (m-TFMA) | CY (N-Allyl) | CY (Diallyl) |
|---|---|---|---|
| Allyl alc. 2.1 mmol | 8 | 61 | 26 |
| Allyl eth. 1 mmol | 7 | 50 | 20 |

Furthermore, the allyl alcohol and ether were assayed:

| DC (allyl alcohol) = | 19 | CY (allyl ether) = | 3 |
|---|---|---|---|
| DC (allyl ether) = | 5 | CY (allyl alcohol) = | 5 |

EXAMPLE 7 m-TFMA Allylation with Allyl Ether+$Pt^{II}$+TPPTS

In a 30-cc Schott tube:
$H_2O$: 5.109 g

PtCl$_2$ (COD): MW=374; 56.1 mg; 0.15 mmol
COD=1,5-cyclooctadiene
TPPTS (0.522 mmol/g): 1.6458 g (0.859 mmol) in water.
  (TPPTS=sodium triphenylphosphinetrisulfonate)
m-TFMA: 1.1442 g; MW=161.1; 7.1024 mmol
allyl ether: MW=98.15; 1.5613 g; 15.907 mmol $$\text{Ratio } \frac{\text{allyl ether}}{\text{m-TFMA}} = 2.24 \quad \frac{\text{PtCl}_2(\text{COD})}{\text{n-TFMA}} = 2.1\%$$
$$\frac{\text{TPPTS}}{\text{PtCl}_2(\text{COD})} = 5.73$$

Reaction time=1 h 30 min at 90° C.; the mixture was then cooled to room temperature and extracted with ethyl acetate, and the phases were separatec after settling had taken place.

The analysis was carried out by gas chromatography on the organic phase, and gave the following results:
DC=18.5%
N-Allyl: CY>95%
Diallyl: CY<0.2%

EXAMPLE 8

Influence of As$_2$O$_3$
Reactants
Phenol: 2 mmol
Pd(Pϕ$_3$)$_4$: 2 mol %
4 h at 90° C. with stirring
1 equivalent of allyl ether: 2 mmol
RESULT

| As$_2$O$_3$ | DC allyl ether | DC (Phenol) | CY (O-Allyl) | CY (C-Allyl) |
|---|---|---|---|---|
| 0% | 61 | 39 | 18 | 41 |
| 5% | 70 | 59 | 23 | 26 |

EXAMPLE 9

Influence of the Catalyst
Reactants
Phenol: 2 mmol
Pd(Pϕ$_3$)$_4$ or Pt(Pϕ$_3$)$_4$: 2 mol %
4 h at 90° C. with stirring
½ equivalent: 1 mmol
RESULT

| Catalyst 2% | As$_2$O$_3$ | DC | DC (Phenol) | CY (O-Allyl) | CY (C-Allyl) |
|---|---|---|---|---|---|
| Pt(Pϕ$_3$)$_4$ | 4.2% | 29 | 12 | 60 | 13 |
| Pd(Pϕ$_3$)$_4$ | 4.5% | 68 | 38 | 30 | 28 |

EXAMPLE 10

(single organic phase)
Reactants
m-TFMA: 2 mmol
Allyl alcohol: 11.2 mmol
Pd(Pϕ$_3$)$_4$: 2 mol %
1 h at 90° C. with stirring
RESULT

| m-TFMA | DC | CY Mono | CY Di |
|---|---|---|---|
|  | 31 | 60 | 13 |

EXAMPLE 11

Two-phase (organic/aqueous)
Reactants
H$_2$O: 5 ml
Allyl alcohol: 3.3 ml (66 mmol)
m-TFMA: 2 ml (16 mmol)
TPPTS: aqueous solution 0.522 mmol/g; T=90° C.
RESULT

| Catalyst (mmol) | TPPTS Metal Mole ratio | Time (h) | DC (%) | TY (%) N-Allyl | TY (%) N-Diallyl |
|---|---|---|---|---|---|
| Pd(OAc)$_2$ (0.16) | 5.2 | 0.75 | 81 | 80 | 1 |
| PtCl$_2$(COD) (0.12) | 6.5 | 5.5 | 94 | 76 | 18 |
| RhCl(COD)/2 (0.19) | 4.5 | 3.5 | 74 | n.d. | n.d. |
| RuCl$_3$ (0.16) | 5.4 | 3.5 | 96 | 78 | 17 |
| NiCl$_2$/NaBH$_4$ (0.2) | 4.6 | 2.5 | 8 | 8 | — | n.d. = reaction product identified but yield not measured

Comment

BRIEF DESCRIPTION OF DRAWING

Pd: The first allylation was very rapid. Sampling of the organic phase enabled it to be assessed (see single Figure).

Pt: Same reaction profile as above but with lower activity.

Ni: The reduction of NiCl$_2$ with sodium borohydride in the presence of TPPTS lead to the formation of Ni(TPPTS)$_4$, of a characteristic red color.

EXAMPLE 12

Organic/Aqueous Two-Phase System
Reactants
Anilide (meta-trifluoromethylacetanilide): 1.08 g (5.32 mmol)
Allyl alcohol/anilide: 5.92
Allyl alcohol: 1.83 g (31.5 mmol)
pd$^{II}$Ac$_2$: 70 mg; MW=224.49; 0.31 mmol; Pd$^{II}$/anilide 5.86%
TPPTS (0.522 mmol/g): 2.39 g (1.2476 mmol)
H$_2$O: 2.35 g
TPPTS/Pd$^{II}$: 4.05
16 h 30 min. at 139° C–140° C.
Anilide: DC<10%
Allyl anilide: TY=7%

EXAMPLE 13—(Comparative)

Organic/Agueous Two-Phase System: Role of the Allyl Unsaturation Test with 1-propanol
Reactants
Aniline (meta-trifluoromethylaniline): 1.2 g (7 mmol)
PtCl$_2$: 53 mg; MW=374; 0.14 mmol;
TPPTS (0.522 mmol/g): 1.6 g (0.84 mmol)

H$_2$O: 5.1 g
1-Propanol: 2.2 g (37 mmol)
Reaction time: 1 h 48 min at 90° C.

The reaction mixture was taken up with ethyl acetate and the latter phase was subjected to an assay by gas chromatography:
Aniline: DC<3%
Propylated aniline: TY=0%

From this result, the need for the presence of the allyl unsaturation was deduced.

EXAMPLE 14

Catalysis by the System Tetrakis(triphenylphosphine)-Pd (Pφ$_3$)$_4$/arsenious anhydride
Amide: 4 mmol
Allyl alcohol: 1.5 ml (22 mmol)
Pd(Pφ$_3$)$_4$: 2% (0.08 mmol)
As$_2$O$_3$: 4% (0.16 mmol)
Manipulations carried out under inert atmosphere
Ar=m—CF$_3$φ—

| Amide | Catalyst | Conditions | DC (amide) (%) | CY |
|---|---|---|---|---|
| ArNHCOCH$_3$ | Pd(Pφ$_3$)$_4$/As$_2$O$_3$ | 90° C. - 17 h | 22 | 100 |
| ArNHCOCH$_3$ | Pd(Pφ$_3$)$_4$ | 140° C. - 17 h | 88 | 90 |
| ArNHCOCH$_3$ | Pd(Pφ$_3$)$_4$/As$_2$O$_3$ | 140° C. - 17 h | 70 | 89 |
| ArNHCOCHCl$_2$ | Pd(Pφ$_3$)$_4$ | 140° C. - 17 h | 86.5 | trace | a) Reaction performed in a 30-ml reactor
b) Reaction performed in a sealed tube.

EXAMPLE 15

Use of Pt(Pφ$_3$)4
REACTION
N-Dichloroacetyl-m-TFMA+allyl alcohol—NAND+H$_2$O
cat.
where
NAND=N-allyl-N-dichloroacetyl-meta-trifluoromethylaniline m-TFMA=meta-trifluoromethylaniline.
Reactants
N-Dichloroacetyl-m-TFMA: 2 mmol
Allyl alcohol: 13 mmol
Pt(Pφ$_3$)$_4$: 2 mol %
4 h at 90° C. with stirring
RESULTS

| As$_2$O$_3$ | DC (Dichloro) | CY (NAND) |
|---|---|---|
| 0% | 11 | 80–100 |
| 8.7% | 14 | 68 |

Comments:
The reaction took place with a relatively low reactivity but a good selectivity. As$_2$O$_3$ has only a slight influence.

EXAMPLE 16

Reactants
Acetanilide: 2 mmol,
Allyl alcohol: 12 mmol
Pd(Pφ$_3$)$_4$: 2.3 mol %
4 h at 90° C. with stirring

RESULTS

| Reactant | DC | CY (estimated) |
|---|---|---|
| p-Methoxyacetanilide | 66 | 10 |
| Acetanilide | 31 | 75 |

EXAMPLE 17

Role of Stannous Chloride
Reactants
m-TFMA: 2 mmol
PtCl$_2$: 2 mol % (0.08 mmol)
4 h at 90° C. with stirring Excess of allyl alcohol, which also plays the part of a solvent, or 1 equivalent dissolved in diglyme. SnCl$_2$ was added in variable amounts.
RESULTS

| Mole ratio Sn/Pt % | Solvent | DC (%) (m-TFMA) | CY (N-Allyl) | CY (Diallyl) |
|---|---|---|---|---|
| 0 | all. alc. | 92.5 | 79 | 6 |
| 1 | all. alc. | 96.5 | 72 | 18 |
| 2 | all. alc. | 100 | 29.5 | 68.5 |
| 0 | diglyme | 22 | 66 | 1 |
| 2 | diglyme | 70 | 77 | 7.5 |
| 3 | diglyme | 76 | 73.5 | 13.5 |

In all cases, the presence of tin chloride was detrimental to the monoallylation although the yields are substantially improved. The unfavorable effect of diglyme on the reaction and the relatively favorable effect on the selectivity were noted.

EXAMPLE 18

Platinum with Another Oxidation Number and Without a Pnictine
The reactions were carried out at 70° C. for 3 h.
m-TFMA=4 mmol
Catalyst=2% (0.08 mmol)

| Catalyst 2% (mol) | DC (m-TFMA) (%) | CY N-Allyl (%) | CY Diallyl (%) |
|---|---|---|---|
| H$_2$PtCl$_6$ | 57.5 | 38 | 0 |

This example shows that coordinating agents of the halide type, especially of the first 3 periods, suffice, in particular, for platinum.

EXAMPLE 19

Catalysis by Pd(Pφ$_3$)$_4$

| Test | Catalyst (2 mol %) | DC (m-TFMA) (%) | CY N-Allyl (%) | CY Diallyl (%) |
|---|---|---|---|---|
| 169-32 | Pd(Pφ$_3$)$_4$ | 22 | 83 | 9 |

Test performed at 70° C. for 3 h using 4 mmol of m-TFMA, 4 mmol of allyl alcohol and 1.2 ml of diglyme.

In order to preserve the qualities of the catalyst, the reactor was charged under an inert atmosphere in a glove box.

Under the same working conditions, PtCl$_2$ gave a DC=22%, CY N-allyl=66% and CY diallyl=1%.

The activity of Pd(Pφ$_3$)4 may hence be compared with that of platinum (II), with a slight gain in N-allyl compound.

EXAMPLE 20
Influence of Arsenious Anhydride

| Test | Catalyst (mol %) | | DC (m-TFMA) (%) | CY N-Allyl (%) | CY Diallyl (%) |
|---|---|---|---|---|---|
| 150-18 (a) | As$_2$O$_3$ | 2% | 9 | 0 | 0 |
| 161-28 (a) | Pd(Pφ$_3$)$_4$ As$_2$O$_3$ | 2% 4% | 100 | 5.5 | 95.5 |
| 169-31 (b) | Pd(Pφ$_3$)$_4$ As$_2$O$_3$ | 2% 4% | 75.5 | 55 | 40.5 |
| 169-32 (b) | Pd(Pφ$_3$)$_4$ | 2% | 22 | 83 | 5 |
| 151-20 (b) | PtCl$_2$ As$_2$O$_3$ | 2% 4% | 13.5 | 45 | 0 |
| 143-7 | PtCl$_2$ | 2% | 22 | 66 | 1 |

(a): m-TFMA = 4 mmol, allyl alcohol = 22 mmol, 70° C., 3 h
(b): m-TFMA = 4 mmol, allyl alcohol = 4 mmol, diglyme 1.2 ml, 70° C., 3 hours It was established that the gain in reactivity provided by adding arsenious anhydride to the reaction medium is observed with Pd(Pφ$_3$)$_4$.

EXAMPLE 21
Role of the Elements of Group V
Reactants
m-TFMA: 2 mmol
Allyl alcohol: 11.2 minol; Pt- or Pd(Pφ$_3$)$_4$: 2 mol %
Cocatalyst: 4 mol %
4 h at 90° C. with magnetic stirring
RESULTS

| Catalyst | DC | CY Mono | CY Di |
|---|---|---|---|
| Pd | 35 | 70 | 8 |
| Pt | 68 | 67 | 28 |
| Pd/As$_2$O$_3$ | 99 | 14 | 89 |
| Pt/As$_2$O$_3$ | 100 | 1 | 99 |
| Pd/Sb$_2$O$_3$ | 22 | 74 | 9 |
| Pt/Sb$_2$O$_3$ | 55 | 64 | 13 |

EXAMPLE 22
Influence of Cocatalysts
Reactants
m-TFMA: 2 mmol
Allyl alcohol: 11.2 mmol
Pd(Pφ$_3$)$_4$: 2 mol %
Cocatalyst: 4 mol %
4 h at 90° C. with magnetic stirring
RESULTS

| Cocata. | DC | CY Mono | CY Di |
|---|---|---|---|
| Bi$_2$O$_3$ | 22 | 82 | 7 |
| B$_2$O$_3$ | 74 | 70 | 31 |

EXAMPLE 23
Role of the Substrate
Reactants
Aniline: 2 mmol
Allyl alcohol: 11.2 mmol
Pd(Pφ$_3$)$_4$: 2 mol %
4 h at 90° C. with stirring
RESULTS

| Reactant | DC | CY Mono (estimated) | CY Di (Estimated) |
|---|---|---|---|
| p-Methoxyaniline | 97 | 12 | 88 |
| Aniline | 97 | 0.2 | 66 |
| p-Nitroaniline | 13 | 95 | 0 |
| m-TFMA | 35 | 70 | 8 |

EXAMPLE 24
Reactants
Aniline: 2 mmol
Allyl alcohol: 11.2 mmol
Pd(Pφ$_3$)$_4$: 2 mol %
As$_2$O$_3$: 4 mol %
4 h at 90° C. with stirring
RESULTS

| Reactant | DC | CY Mono (estimated) | CY Di (Estimated) |
|---|---|---|---|
| p-Methoxyaniline | 100 | 1 | 100 |
| Aniline | 99 | 0.6 | 90 |
| p-Nitroaniline | 40 | 100 | 0 |
| m-TFMA | 99 | 14 | 89 |

EXAMPLE 25
Kinetics
Reactants
m-TFMA (meta-trifluoromethylaniline): 2 mmol
Allyl alcohol: 11.2 mmol
Pd(Pφ$_3$)$_4$: 2 mol %
As$_2$O$_3$: 5 mol %
RESULTS

| m-TFMA | DC | CY Mono | CY Di |
|---|---|---|---|
| 4 h - 90° C. | 99 | 14 | 89 |
| 3 h - 90° C.* | 100 | 6 | 100 |
| 2 h - 90° C. | 100 | 19 | 93 |
| 1 h - 90° C. | 100 | 2 | 100 |

*(4% As$_2$O$_3$)

EXAMPLE 26
Temperature Reduction
Reactants
m-TFMA (meta-trifluoromethylaniline): 2 mmol
Allyl alcohol: 11.2 mmol
Pd(Pφ$_3$)$_4$: 2 mol %
As$_2$O$_3$: 4 mol %
RESULTS

| m-TFMA | DC | CY Mono | CY Di |
|---|---|---|---|
| 1 h - 90° C.* | 100 | 2 | 100 |
| 1 h - 80° C. | 100 | 11 | 87 |
| 1 h - 70° C. | 99 | 12 | 89 |
| 1 h - 60° C. | 99 | 10 | 90 |

*(As$_2$O$_3$ 5.4%)

We claim:
1. A process for allylating a nucleophile, comprising reacting said nucleophile with an allyl derivative in the presence of a catalyst in an aqueous phase containing at least one element of group VIII of the Classification of the elements;

wherein said nucleophile is a compound of formula (V):

(R)$_n$Ar—Y—H     (V)

wherein:
Ar represents a monocyclic aromatic radical which is homocyclic or heterocyclic or Ar represents a polycyclic aromatic radical which may be fused or nonfused and is homo- or heterocyclic,
R represents at least one substituent selected independently from the group consisting of hydrogen, chlorine, bromine, saturated or unsaturated and optionally substituted linear, branched or cyclic alkyl radicals, ether, and optionally substituted radicals selected from alkoxy, aryloxy, amino, hydroxyl, carboxylate, acyloxy, ester, amido, nitrile and acid radicals;
n is an integer greater than or equal to 1,
Y represents an oxygen atom or a group NR' with R' representing an alkyl radical containing 1 to 10 carbon atoms or a hydrogen atom.

2. The process as claimed in claim 1, wherein said allyl derivative contains an ether group or a mixture wherein at least one allyl derivative contains an ether group.

3. The process as claimed in claim 1, wherein said allyl derivative contains an alcohol group or a mixture wherein at least one allyl derivative contains an alcohol group.

4. The process as claimed in claim 1, wherein said allyl derivative corresponds to formula (III):

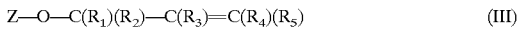

Z—O—C(R$_1$)(R$_2$)—C(R$_3$)=C(R$_4$)(R$_5$)     (III)

wherein:
R$_1$ represents a hydrogen or an alkyl radical,
R$_2$ represents a hydrogen or an alkyl radical,
R$_3$ represents a hydrogen or an alkyl radical,
R$_4$ represents a hydrogen or an alkyl radical,
R$_5$ represents a hydrogen or an alkyl radical, and
Z represents a hydrogen atom or a residue derived from an alcohol by removal of a hydroxyl group.

5. The process as claimed in claim 4 wherein at least one of R$_1$, R$_2$ R$_3$, R$_4$ and R$_5$ contain 1 or 2 carbon atoms.

6. The process as claimed in claim 1, wherein Y represents the group NR' and R' contains 1 to 6 carbon atoms.

7. The process as claimed in claim 1, wherein n is selected from 1, 2, 3, or 4.

8. The process as claimed in claim 1, wherein said compound of formula (V) is selected from the deactivated anilines of formula (II):

A—Ar—N—H$_2$     (II)

where:
A represents a substituent, or a hydrogen atom;
Ar has the same meaning as defined above.

9. The process as claimed in claim 1, wherein said compound of formula (V) is selected from phenols having formula IV:

(R)$_n$AR—O—H     (IV)

wherein:
R, Ar and n have the same meaning as defined above.

10. The process as claimed in claim 1, wherein the nucleophile to be allylated possesses at least one halogen and said element of group VIII is platinum.

11. The process as claimed in claim 1, wherein the element of group VIII is a platinum ore metal.

12. The process as claimed in claim 1, wherein the element of group VIII is palladium.

13. The process as claimed in claim 1, wherein said reaction occurs in the presence of at least one coordinating agent.

14. The process as claimed in claim 13, wherein said coordinating agent is a triphenylphosphine-trisulfonate.

15. The process as claimed in claim 13, wherein said coordinating agent is a pnictine.

16. The process as claimed in claim 15, wherein said pnictine is a trialkylphosphine or a triphenylphosphine.

17. The process as claimed in claim 16, wherein the pnictine is a trialkylphosphine.

18. The process as claimed in claim 13 wherein said coordinating agent and said element of group VIII are in the form of tetrakis(phosphine)-metal.

19. The process as claimed in claim 13, wherein said coordinating agent is a water-soluble phosphine.

20. The process as claimed in claim 13, wherein the reaction takes place in a medium containing 2 immiscible liquid phases, one of which is said aqueous phase which contains said coordinating agent.

21. The process as claimed in claim 20, wherein, after the allylation reaction, the aqueous phase is recovered and reused for a further allylation operation.

22. A process as claimed in claim 1, wherein said catalyst further contains an oxide of an element of group V B of the Periodic Classification of the elements.

23. The process as claimed in claim 22, wherein said element of group V B is in the trivalent state.

24. The process as claimed in claim 23, wherein said element of group V B is arsenic.

25. A process for the synthesis of N-(allyl)acylaniline, comprising reacting a compound of the formula:

A—Ar—N(Ac)—H wherein:
Ar represents a monocyclic aromatic radical which may be homocyclic or heterocyclic or Ar represents a polycyclic aromatic radical which may be fused or nonfused and may also be homo- or heterocyclic, and
Ac represents an acyl radical;
with a compound of formula (III)

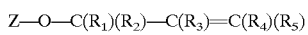

Z—O—C(R$_1$)(R$_2$)—C(R$_3$)=C(R$_4$)(R$_5$)     (III)

wherein:
R$_1$ represents a hydrogen or an alkyl radical,
R$_2$ represents a hydrogen or an alkyl radical,
R$_3$ represents a hydrogen or an alkyl radical,
R$_4$ represents a hydrogen or an alkyl radical,
R$_5$ represents a hydrogen or an alkyl radical, and
Z represents a hydrogen atom or a residue derived from an alcohol by removal of a hydroxyl group;
in the presence of a catalyst containing at least one element of group VIII of the Periodic Classification of the elements.

26. The synthesis process as claimed in claim 25, wherein Ac is an acyl group for which the corresponding acid possesses at least one halogen in the α-position with respect to the acid function and said element of VIII is platinum.

27. The synthesis process as claimed in claim 25, wherein the acyl radical Ac is a substituted or unsubstituted radical having 1 to 6 carbon atoms.

28. The synthesis process as claimed in claim 25, wherein the acyl radical Ac has the formula:

—OC—R$_6$ wherein:

R$_6$ is an alkyl radical optionally mono-, di- or trihalogenated and wherein said alkyl radical may carry compatible monovalent functions.

29. The synthesis process as claimed in claim 25, wherein said catalyst further contains an oxide of an element of group V B of the Periodic Classification of the elements.

* * * * *

UNITED STATES PATENT AND TRADEMARK OFFICE
CERTIFICATE OF CORRECTION

PATENT NO.   : 5,986,137
DATED        : November 16, 1999
INVENTOR(S)  : Jean-Michel GROSSELIN et al.

It is certified that error appears in the above-identified patent and that said Letters Patent is hereby corrected as shown below:

Title page, Item [57], in the Abstract, Line 6, "lone" should read --one--.

Claim 1, column 17, line 8, "may be" should read --is--.

Claim 5, column 17, line 42, after "R $_2$", insert --,--.

Signed and Sealed this

Third Day of April, 2001

*Attest:*

NICHOLAS P. GODICI

*Attesting Officer*   Acting Director of the United States Patent and Trademark Office